United States Patent [19]
Douglas et al.

[11] Patent Number: 6,048,352
[45] Date of Patent: Apr. 11, 2000

[54] DISPOSABLE ELEMENT FOR USE IN A BODY FLUID SAMPLING DEVICE

[75] Inventors: Joel S. Douglas, Santa Clara; Jeffrey N. Roe, San Ramon; Ryszard Radwanski, Morgan Hill; Brent G. Duchon, San Jose; Michael J. Sanchez, Mountain View; Henry M. Grage, Danville, all of Calif.

[73] Assignee: Mercury Diagnostics, Inc., Palo Alto, Calif.

[21] Appl. No.: 08/857,335

[22] Filed: May 16, 1997

Related U.S. Application Data

[60] Provisional application No. 60/017,133, May 17, 1996, provisional application No. 60/019,918, Jun. 14, 1996, provisional application No. 60/023,658, Aug. 1, 1996, and provisional application No. 60/025,340, Sep. 3, 1996.

[51] Int. Cl.[7] ...................................................... A61B 5/00
[52] U.S. Cl. .......................................... 606/181; 600/583
[58] Field of Search ..................................... 606/181, 182, 606/183; 600/583

[56] References Cited

U.S. PATENT DOCUMENTS

| D. 254,444 | 3/1980 | Levine . |
| 4,360,016 | 11/1982 | Sarrine . |
| 4,503,856 | 3/1985 | Cornell et al. . |
| 4,517,978 | 5/1985 | Levin et al. . |
| 4,622,974 | 11/1986 | Coleman et al. . |
| 4,627,445 | 12/1986 | Garcia et al. . |

(List continued on next page.)

FOREIGN PATENT DOCUMENTS

| 0453283 | 10/1991 | European Pat. Off. . |
| 3708031 | 11/1987 | Germany . |
| WO 8504089 | 9/1985 | WIPO . |
| WO 9510223 | 4/1995 | WIPO . |
| WO 9743962 | 11/1997 | WIPO . |

OTHER PUBLICATIONS

Ash, et al., "A Subcutaneous Capillary Filtrate. . . ," ASAIO Journal, 1993, pp. M699–M705.
Ash, et al., "Subcutaneous Capillary Filtrate. . . " ASAIO Journal, 1992, pp. M416–M420.
Critical Reviews in Biochemical Engineering, vol. 18, issue 1, 1990, pp. 29–54.
Brace, et al., "Reevaluation of the needle. . . ," Amer Jrnal of Phy, v 229, 1975, pp. 603–607.
Ginsberg., "An Overview of Minimally. . . ," Clinical Chem, v 38, 1992, pp. 1596–1600.
Janle–Swain, et al., "Use of Capillary. . . ," Trans Am Soc Artif Intern Organs, 1987, pp. 336–340.
Kayashima, et al., "Suction effusion fluid from. . . ," Amer Phys Soc, 1992, pp. H1623–1626.
Korthuis, et al., "Interstitium & Lymphatic Techniques," pp. 326–327.
Turner, et al., "Diabetes Mellitus: Biosensors for. . . ," Biosensors, 1985, pp. 85–115.

*Primary Examiner*—William Lewis
*Attorney, Agent, or Firm*—Burns, Doane, Swecker & Mathis, L.L.P.

[57] ABSTRACT

A disposable lancing element is adapted for use in a lancing device for making an incision through a user's skin. The lancing element includes a body which defines a longitudinal axis, and has a skin-lancing member projecting from a front end thereof. A capillary tube is mounted in the body in laterally spaced relationship to the skin-lancing member and is slidable longitudinally relative to the body so as to be extended forwardly past the skin-lancing member. The body includes a plurality of circumferentially spaced, radially outwardly projecting bosses formed thereon for guiding the disposable element installation in a carrier element. The skin-lancing member may comprise a plurality of needles or barbs arranged in parallel side-by-side relationship. In lieu of a skin-lancing member, the disposable element may possess a longitudinal through-hole for conducting a skin-piercing laser light beam or pressurized fluid. A capillary tube may have an outwardly flared lower (inlet) end. A capillary tube may possess a sensor for sensing a level of fluid rising therein.

13 Claims, 5 Drawing Sheets

U.S. PATENT DOCUMENTS

| | | |
|---|---|---|
| 4,637,403 | 1/1987 | Garcia et al. . |
| 4,648,408 | 3/1987 | Hutcheson et al. . |
| 4,653,511 | 3/1987 | Goch . |
| 4,653,513 | 3/1987 | Dombrowski . |
| 4,658,821 | 4/1987 | Chiodo et al. . |
| 4,685,463 | 8/1987 | Williams . |
| 4,787,398 | 11/1988 | Garcia et al. . |
| 4,790,979 | 12/1988 | Terminiello et al. . |
| 4,805,623 | 2/1989 | Jobsis . |
| 4,850,973 | 7/1989 | Jordan et al. . |
| 4,858,607 | 8/1989 | Jordan et al. . |
| 4,873,993 | 10/1989 | Meserol et al. . |
| 4,883,068 | 11/1989 | Dechow . |
| 4,920,977 | 5/1990 | Haynes . |
| 4,924,879 | 5/1990 | O'Brien . |
| 4,953,552 | 9/1990 | DeMarzo . |
| 4,976,724 | 12/1990 | Nieto et al. . |
| 4,994,068 | 2/1991 | Hufnagle . |
| 5,002,054 | 3/1991 | Ash et al. . |
| 5,014,718 | 5/1991 | Mitchen . |
| 5,029,583 | 7/1991 | Meserol et al. . |
| 5,054,499 | 10/1991 | Swierczek . |
| 5,066,859 | 11/1991 | Karkar et al. . |
| 5,070,886 | 12/1991 | Mitchen et al. . |
| 5,163,442 | 11/1992 | Ono . |
| 5,165,418 | 11/1992 | Tankovich . |
| 5,201,324 | 4/1993 | Swierczek . |
| 5,217,480 | 6/1993 | Haber et al. . |
| 5,231,993 | 8/1993 | Haber et al. . |
| 5,277,198 | 1/1994 | Kanner et al. . |
| 5,318,584 | 6/1994 | Lange et al. . |
| 5,320,607 | 6/1994 | Ishibashi . |
| 5,368,047 | 11/1994 | Suzuki et al. . |
| 5,395,387 | 3/1995 | Burns . |
| 5,402,798 | 4/1995 | Swierczek et al. . |
| 5,569,212 | 10/1996 | Brown . |
| 5,582,184 | 12/1996 | Erickson et al. . |
| 5,611,809 | 3/1997 | Marshall et al. . |
| 5,628,309 | 5/1997 | Brown . |
| 5,628,764 | 5/1997 | Schraga . |

6,048,352

DISPOSABLE ELEMENT FOR USE IN A BODY FLUID SAMPLING DEVICE

PRIOR APPLICATIONS

This application claims benefit of provisional applications Ser. No. 60/017,133 filed May 17, 1996; 60/019,918 filed Jun. 14, 1996; 60/023,658 filed Aug. 1, 1996; 60/025,340 filed Sep. 3, 1996; the disclosures of which are incorporated herein by reference.

The present invention is related to inventions disclosed in the following concurrently filed, commonly assigned U.S. applications: Ser. No. 08/857,680, entitled "Body Fluid Sampling Device and Methods of Use" (attorney docket No. 018176-039); Ser. No. 08/858,045, entitled "Methods and Apparatus for Sampling Body Fluid" (attorney docket 018176-057); Ser. No. 08/858,042, entitled "Methods and Apparatus for Sampling and Analyzing Body Fluid" (attorney docket 018176-059); and Ser. No. 08/858,043, entitled "Methods and Apparatus for Expressing Body Fluid From an Incision" (attorney docket 18176-060). The disclosures of those applications are incorporated herein by reference.

FIELD OF THE INVENTION

The present invention relates to lancing devices and methods for obtaining samples of blood and other fluids from the body for analysis or processing.

BACKGROUND OF THE INVENTION

Many medical procedures in use today require a relatively small sample of blood, in the range of 5–50 $\mu$L. It is more cost effective and less traumatic to the patient to obtain such a sample by lancing or piercing the skin at a selected location, such as the finger, to enable the collection of 1 or 2 drops of blood, than by using a phlebotomist to draw a tube of venous blood. With the advent of home use tests such as self monitoring of blood glucose, there is a requirement for a simple procedure which can be performed in any setting by a person needing to test.

Lancets in conventional use generally have a rigid body and a sterile needle which protrudes from one end. The lancet may be used to pierce the skin, thereby enabling the collection of a blood sample from the opening created. The blood is transferred to a test device or collection device. Blood is most commonly taken from the fingertips, where the supply is generally excellent. However, the nerve density in this region causes significant pain in many patients. Sampling of alternate site, such as earlobes and limbs, is sometimes practiced to access sites which are less sensitive. These sites are also less likely to provide excellent blood samples and make blood transfer directly to test devices difficult.

Repeated lancing in limited surface areas (such as fingertips) results in callous formation. This leads to increased difficulty in drawing blood and increased pain.

To reduce the anxiety of piercing the skin and the associated pain, many spring loaded devices have been developed. The following two patents are representative of the devices which were developed in the 1980's for use with home diagnostic test products.

U.S. Pat. No. 4,503,856, Cornell et al., describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

Levin et al. U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In institutional settings, it is often desirable to collect the sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

Haynes U.S. Pat. No. 4,920,977 describes a blood collection assembly with lancet and microcollection tube. This device incorporates a lancet and collection container in a single device. The lancing and collection are two separate activities, but the device is a convenient single disposable unit for situations when sample collection prior to use is desirable. Similar devices are disclosed in Sarrine U.S. Pat. No. 4,360,016, and O'Brien U.S. Pat. No. 4,924,879.

Jordan et al. U.S. Pat. Nos. 4,850,973 and No. 4,858,607, disclose a combination device which may be alternatively used as a syringe-type injection device and a lancing device with disposable solid needle lancet, depending on configuration.

Lange et al. U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

Suzuki et al. U.S. Pat. No. 5,318,047, Dombrowski U.S. Pat. No. 4,654,513 and Ishibashi et al. U.S. Pat. No. 5,320,607 each describe suction-type blood samplers. These devices develop suction between the lancing site and the end of the device when the lancet holding mechanism withdraws after piercing the skin. A flexible gasket around the end of the device helps seal the end around the puncture site until adequate sample is drawn from the puncture site or the user pulls back on the device.

Garcia et al. U.S. Pat. No. 4,637,403 discloses a combination lancing and blood collection device which includes a capillary passage aligned with a lancet to conduct body fluid to a separate test strip in the form of a microporous membrane. Since the needle and capillary passage are integral, their cross sectional areas cannot be independently sized. Also, the needle must remain in contact with the wound to enable body fluid to be drawn up.

International Publication Number WO95/10223, Erickson et al., describes a means of collecting and measuring body fluids. This system uses a disposable lancing and suction device with a spacer member which compresses the skin around the lance/needle.

Single use devices have also been developed for single use tests, i.e. home cholesterol testing, and for institutional use to eliminate cross-patient contamination multi-patient use. Crossman et al. U.S. Pat. No. 4,869,249, and Swierczek U.S. Pat. No. 5,402,798, also disclose disposable, single use lancing devices. Currently, single use devices utilize a single skin-lancing member, e.g., a single needle, to create an incision through which body fluid can be extracted. In order to increase the amount of fluid extraction, such devices require that the width and/or length of the needle be increased. However, increased width or length of penetration is accompanied by an increase in pain experienced by the user.

The disclosures of the above patents are incorporated herein by reference.

It is difficult to maneuver the capillary tubes of prior art devices into position for drawing-in body fluids, making the utility of such capillary tubes somewhat limited.

An object of this invention is to improve the versatility of a capillary passage wherein its diameter can be sized independently of a needle diameter, and wherein it can be better positioned for contacting a sample of body fluid.

A further object of the invention is to provide a disposable element which is self-guiding when being installed in a lancet carrier, and which is more stable once installed.

Yet another object is to enable the amount of body fluid expressed from the user's skin to be increased without an accompanying increase in pain.

Another object of this invention is to provide a method which can result in a sample of body fluid, i.e., either blood or interstitial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method which can draw a small but adjustable sample, i.e. 3 $\mu$L for one test device and 8 $\mu$L for another test device, as appropriate.

Another object of this invention is to provide a method by which the drawn sample is collected and may be easily presented to a testing device, regardless of the location of the sample site on the body. This approach helps with infection control in that multiple patients are not brought in contact with a single test instrument; only the sampling device with a disposable patient-contact portion is brought to the test instrument. Alternatively, the disposable portion of a test device may be physically coupled with the sampler so the sample can be brought directly into the test device during sampling. The test device may then be read in a test instrument if appropriate or the testing system can be integrated into the sampler and the test device can provide direct results displayed for the patient.

It is a further object of the invention to provide a device for minimally invasive sampling comprising a reusable sampler and disposable lancet and sample collection test member.

SUMMARY OF THE INVENTION

The present invention relates to a disposable lancing element adapted for use in a lancing device for making an incision through a user's skin. The disposable lancing element comprises a skin-lancing member and a capillary tube mounted in laterally spaced relationship to the skin-lancing member. The capillary tube or the skin-lancing member is slidable longitudinally relative to the other.

The capillary tube and skin-lancing member are mounted in a body. The body preferably includes a plurality of circumferentially spaced, radially outwardly projecting bosses formed thereon, one of the bosses being spaced longitudinally from two others of the bosses.

Another aspect of the invention relates to a disposable element adapted for use in a device for perforating a user's skin. The disposable element comprises a body defining a longitudinal axis. The body includes a longitudinal through-hole extending completely therethrough for conducting a skin-piercing laser light, and a mediating lens. A capillary tube is mounted in the body in radially spaced relationship to the through-hole.

Another aspect of the invention relates to a disposable lancing element adapted for use in a lancing device for making an incision through a user's skin. The disposable lancing element comprises a body defining a longitudinal axis, and a plurality of skin-lancing members projecting forwardly by equal distances from a front end of a body. The skin-lancing members are laterally spaced apart and extend mutually parallel.

Yet another aspect of the invention relates to a disposable lancing element adapted for use in a lancing device for making an incision. The disposable lancing element comprises a body defining a longitudinal axis. The body includes a plurality of bosses that are circumferentially spaced from one another and extend radially outwardly. One of the bosses is spaced longitudinally from others of the bosses. An arm projects rearwardly from a rear end of the body, and a skin-lancing member projects forwardly from a front end of the body.

Further aspects of the invention relate to a capillary tube having an outwardly flared lower end, and a capillary tube possessing a fluid sensor.

BRIEF DESCRIPTION OF THE DRAWING

The objects and advantages of the invention will become apparent from the following detailed description of preferred embodiments thereof in connection with the accompanying drawing in which like numerals designate like elements and in which.

DETAILED DESCRIPTION OF PREFERRED EMBODIMENTS OF THE INVENTION

Figure 1:
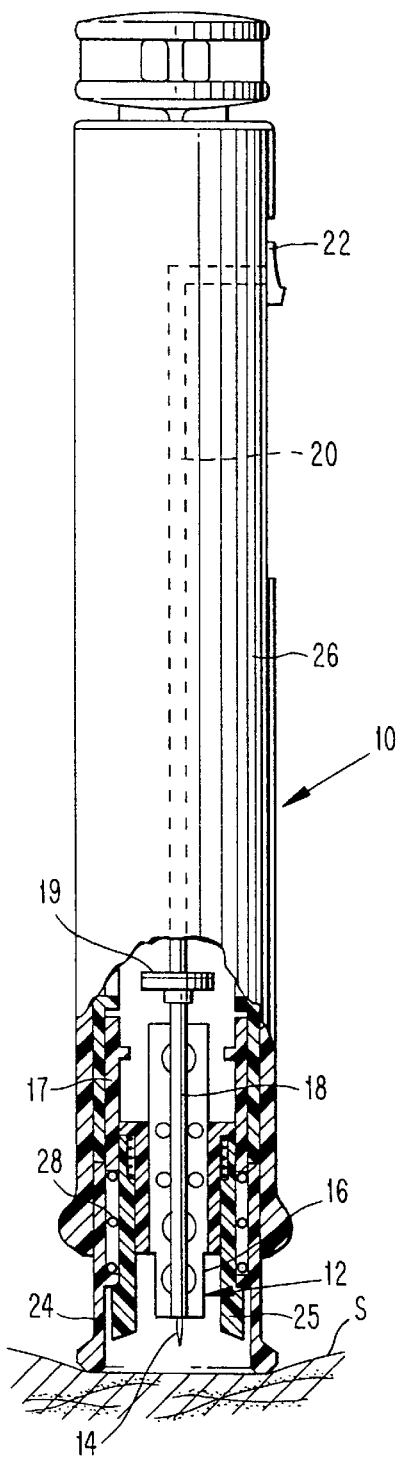
FIG. 1 is a side elevational view, partially in section schematically depicting a disposable element according to the present invention, the disposable element being disposed in a retracted condition.
Figure 2:
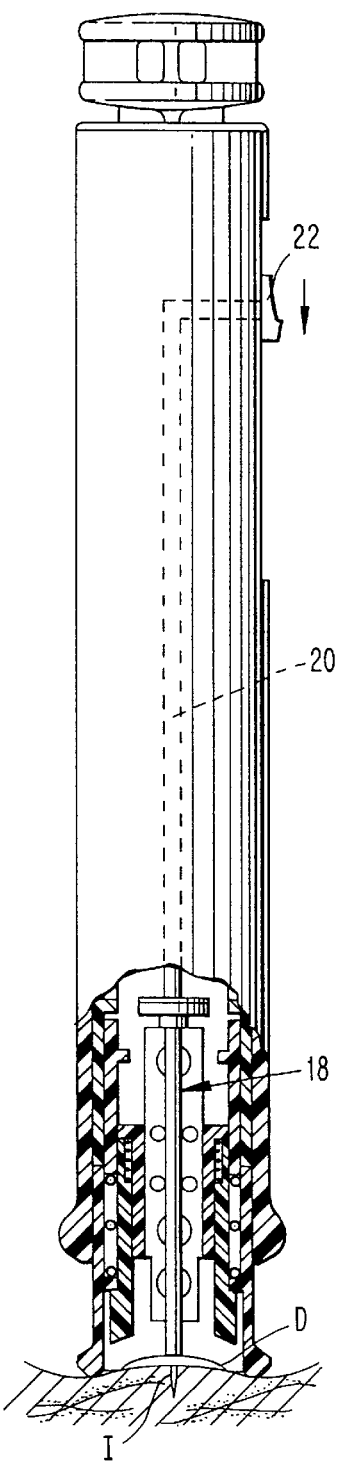
FIG. 2 is a view similar to FIG. 1 after the disposable element has cut an incision, and a capillary tube of the disposable element has been extended forwardly to draw up body fluid from the incision.

In FIGS. 1 and 2 there is disclosed a lancing device 10 adapted to make an incision through a skin surface S for taking a sample of body fluid. A disposable lancet 12 (hereinafter referred to as a "disposable") which carries a skin-lancing member in the form of a needle 14 is displaced toward the skin surface by the release of a cocked spring (not shown) and then is rapidly retracted by another spring. The disposable 12 includes a body 16 which carries not only the needle 14, but also a capillary tube 18. The capillary tube is mounted by friction-fit and is downwardly slidable relative to the body 16 in response to manual downward displacement of a pusher 20 which possesses an exposed actuator knob 22.

The present invention relates to the disposable 12, but a brief description of the device 10 is in order. Details of the housing and a unit 30 for supporting the disposable 12 can be found in commonly assigned, concurrently filed Application Nos. 08/857,680 and 08/858,043 (attorney docket 018176-039 and 018176-060), the disclosures of which are incorporated herein by reference. The disposable 12 is mounted in a lancet carrier 13 which is situated telescopingly within a cylindrical stimulator sleeve 24. The sleeve is slidable longitudinally relative to a housing 26 of the device, and is biased downwardly, or forwardly, by a spring 28. Following the forming of an incision I in the skin, the housing is repeatedly pushed downwardly, whereupon the sleeve depresses a ring of body tissue in surrounding relationship to the incision, causing the incision to bulge while spreading apart the sides of the incision. Consequently, a drop of body fluid such as blood or interstitial fluid is formed at the open end of the incision, even if the incision I has been made in a region of the body where the supply of body fluid is relatively low as compared to, say, the fingertip region.

Once the drop D has been created, the pusher 20 is displaced to push the capillary tube downwardly relative to the body 16 to a state where the lower end of the capillary tube can be dipped into the drop of body fluid to obtain a sample. The pusher is then released and ascends. The fluid sample can be transferred to a test strip which is separate from the capillary tube, or to a test strip 19 that is affixed to the upper capillary tube.

A removable unit 30 of the device 10 (FIG. 3) is comprised of the sleeve 24, the lancet carrier 13, an inner sleeve 25 which supports the lancet carrier 13 for sliding motion, an adapter 17 for releasably securing the unit in the housing 26, and biasing springs 28 and 29.

The lancet carrier 13 includes a pair of downwardly inclined, upwardly facing guide ramps 40 formed on its inner surface for guiding the disposable 12. Lower ends of the guide ramps 40 intersect to form an upwardly open recess 42. Three radially outwardly projecting bosses are formed on the lancet carrier, namely a pair of diametrically opposed upper guide bosses 31 lying on a common plane, and a lower locking boss 33 which is circumferentially spaced by ninety degrees relative to each of the upper bosses 31.

Figure 3:
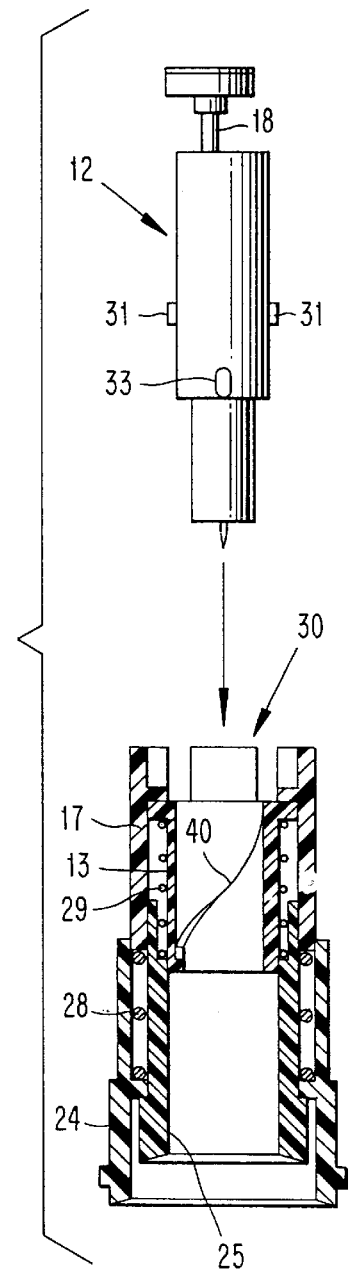
FIG. 3 is an exploded view of a disposable element according to the present invention being inserted into a disposable-receiving unit of a lancing device, the unit being depicted in longitudinal section.
Figure 4:
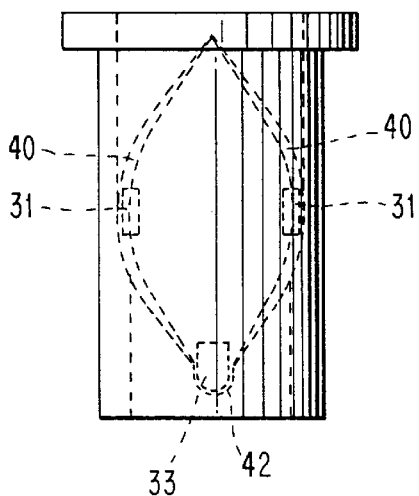
FIG. 4 is a side elevational view of a lancet carrier adapted to receive the disposable element according to the present invention.

To install a disposable into the unit 30, the unit 30 is pulled downwardly from the housing, and a disposable 12 is dropped downwardly into the carrier (see FIG. 3). In so doing, the upper bosses 36 of the disposable ride along the guide ramps 40 of the lancet carrier to bring the lower boss 33 into alignment with the recess 42 of the carrier. When the lower boss enters the recess 42, the capillary tube 18 of the disposable is oriented in a specific relationship with respect to the unit 30. Also, the bosses 31, 33 stabilize the disposable within the carrier.

The unit 30 is then reinstalled by being pushed longitudinally upwardly into the front end of the housing 12. Since the upper end of the capillary tube 18 projects slightly upwardly past the upper end of the body 16 of the disposable, it slightly raises the pusher in order to deactivate a locking mechanism (not shown) to permit the device to be armed.

Figure 5:
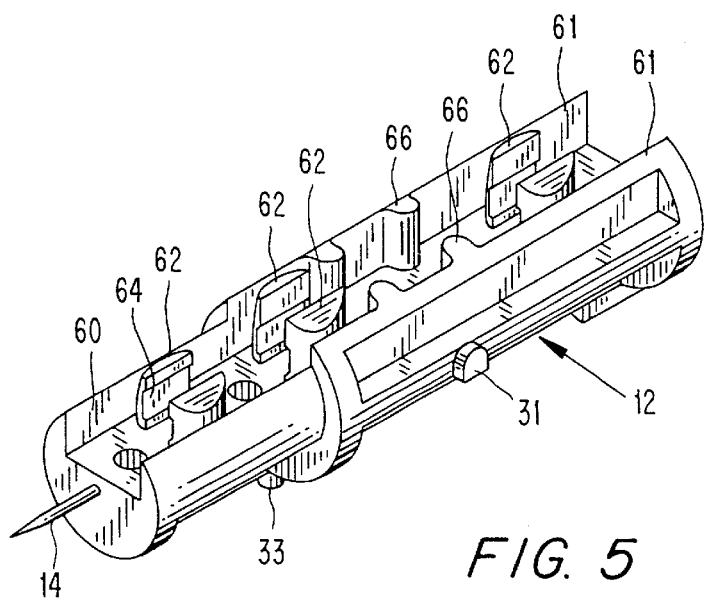
FIG. 5 is a perspective view of one form of disposable element according to the present invention, with the capillary tube thereof removed.
Figure 6:
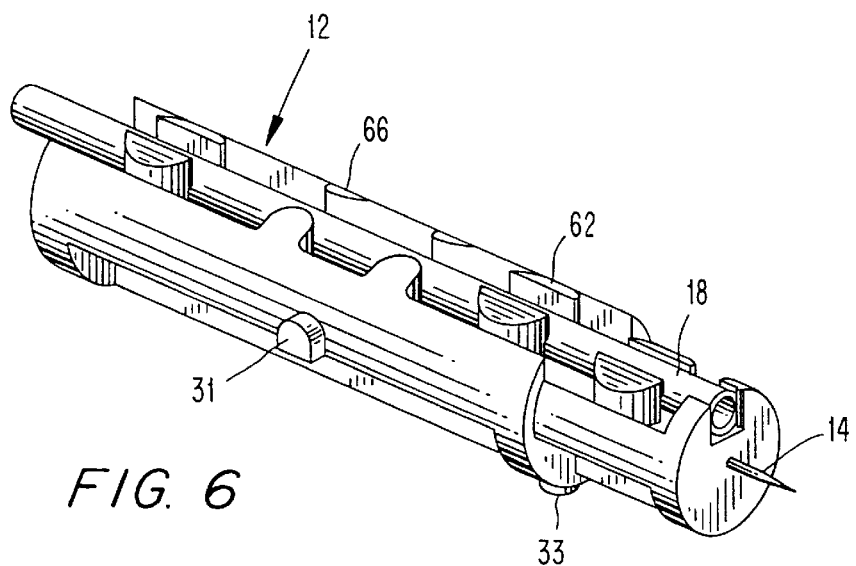
FIG. 6 is another perspective view of the disposable element depicted in FIG. 5, with the capillary tube installed.

The disposable 12 shown in FIGS. 5 and 6 includes a slot 60 formed by a pair of walls 61, the slot extending longitudinally along the body. Disposed within the slot 60 are a plurality of pairs of opposed clamping fingers 62 which are configured to frictionally grip the capillary tube 18 and retain the tube 64 in an orientation parallel to the longitudinal axis of the disposable. The clamping fingers 62 include recesses 64 in which the capillary tube is seated, to prevent the tube from being dislodged from the body in a radial direction. The capillary tube can be installed by being pushed radially into the slot, to spread apart the fingers 62 which eventually snap-back to capture the capillary tube. If desired, radially outer ends of the clamping fingers could be bevelled to promote the spreading action.

A plurality of pairs of opposed guide fingers 66 are disposed along the slot 60 to aid in guiding the capillary tube during its insertion. If desired, the capillary tube could be installed by being pushed longitudinally along the slot instead of being radially snapped-in.

The clamping fingers 62, guide fingers 66, and bosses 31, 33 are molded of one piece with the body, preferably of plastic.

Figure 7:
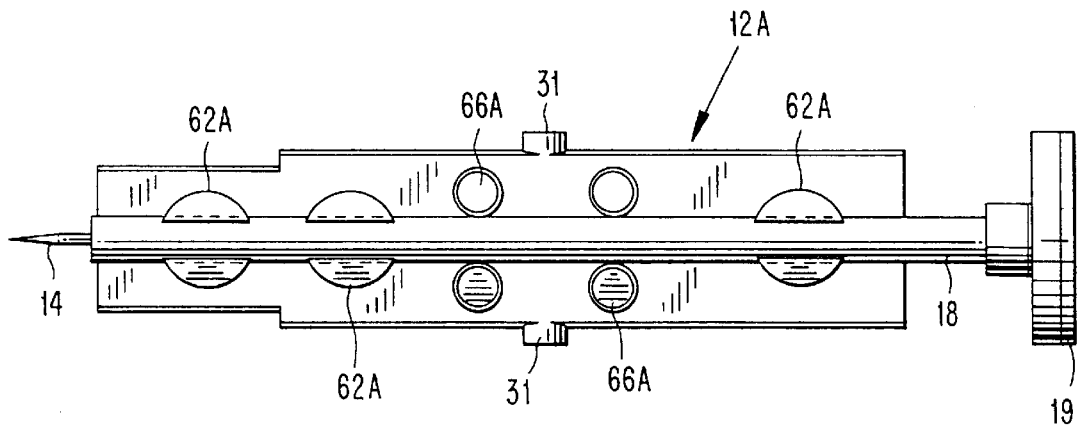
FIG. 7 is a plan view of another form of disposable element according to the present invention.
Figure 8:
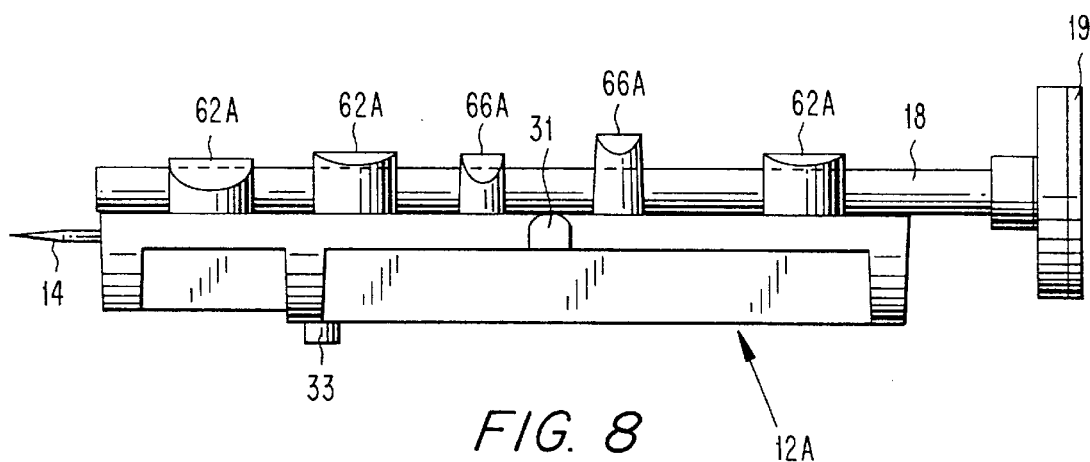
FIG. 8 is a side elevational view of the disposable element depicted in FIG. 7.

A modified form of disposable 12A is depicted in FIGS. 7 and 8 wherein the side walls 61 are removed. Otherwise, the disposable 12A functions in the same manner as the previously-described disposable 12. That is, the clamping fingers 62A and guide fingers 66A frictionally support the capillary tube.

Figure 9:
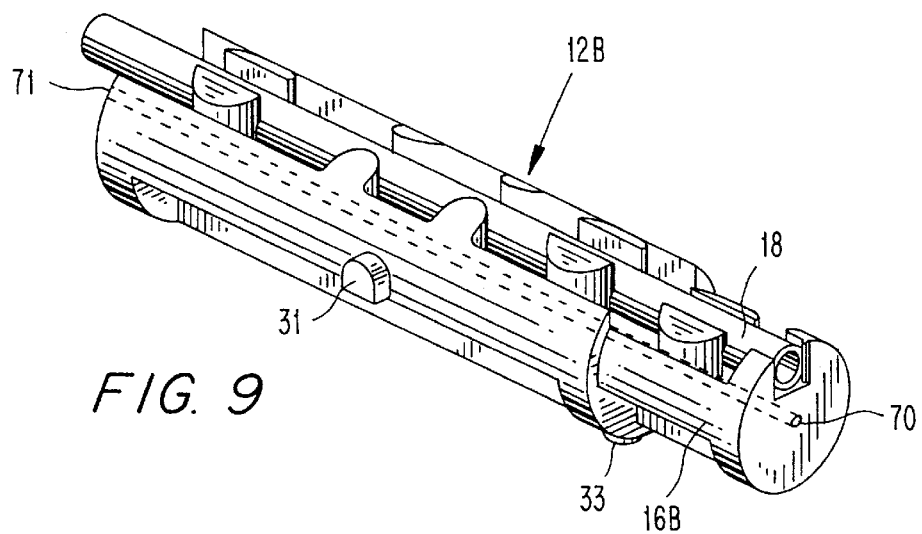
FIG. 9 is a perspective view of another form of disposable element according to the present invention.

Another modified form of disposable 12B is depicted in FIG. 9 wherein no needle is employed. Rather, a center axial through-hole 70 is formed through the body 16B and is adapted to conduct a skin-piercing medium such as laser light, or a stream of pressurized fluid (i.e., gas or liquid) for perforating a user's skin. For example, a laser generator (not shown) could be mounted in the housing to become aligned with the hole 70 when the disposable has been installed. A mediating lens 71 is mounted at an upper end of the hole 70 to disperse the laser beam. The pressurized liquid or gas (possibly with abrasive particles entrained therein) could be emitted from known auto-inject devices used for injecting insulin directly through the skin (with the insulin eliminated therefrom, of course).

Figure 10:
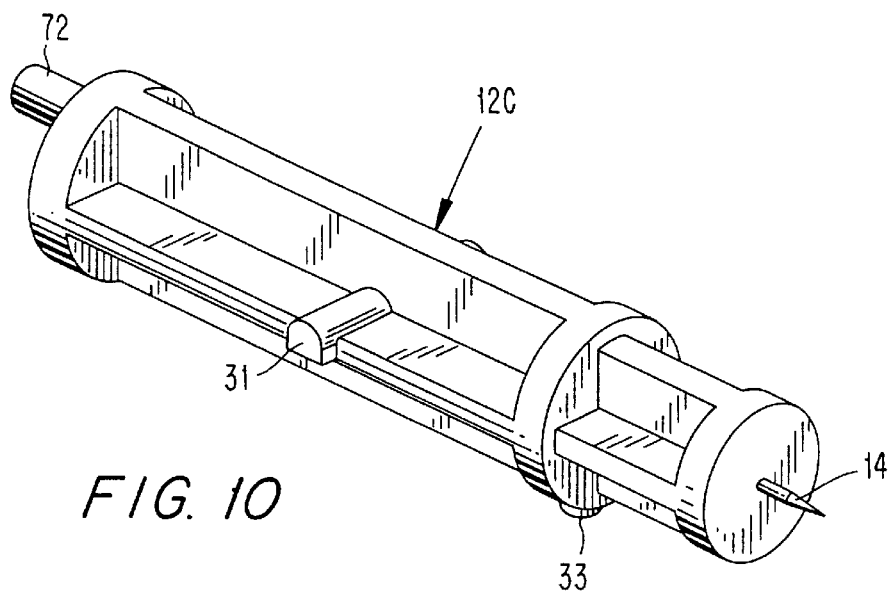
FIG. 10 is a perspective view of still another form of disposable element according to the present invention.

Another modified disposable 12C is depicted in FIG. 10 wherein no capillary tube is utilized. However, the rear or upper end of the body includes an integrally molded arm 72 located in the same position as a capillary tube would have been. That projection 72 functions in the same manner as the upper end of a capillary tube, i.e. to raise the pusher 20 in order to deactivate a locking mechanism of the arming system, as mentioned above.

Figure 11:
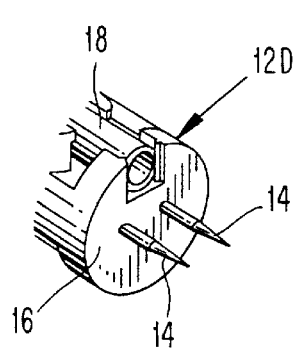
FIG. 11 is a fragmentary perspective view of a form of disposable element having two needles.
Figure 12:
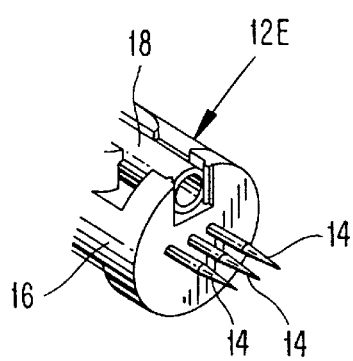
FIG. 12 is a view similar to FIG. 11 of a disposable element having three needles.

In FIGS. 11 and 12, respective modifications 12D, 12E of the needle-type of disposable are shown, where more than one needle 14 is deployed.

In FIG. 11, two parallel, laterally spaced needles 14 are deployed on opposite sides of the center axis, and in FIG. 12 a third needle has been added which coincides with the center axis. The needles 14 project forwardly from the body 16 by the same distance. By making more than one incision through a user's skin, the amount of the body fluid sample can be appreciably increased without increasing the amount of pain experienced by the user. That eliminates the need to resort to a more painful, higher gauge needle in order to increase the sample amount.

It will be appreciated that the features disclosed in connection with FIGS. 9, 11 and 12, namely, the provision of an axial through hole 70 and additional needles 14, could be employed in combination with the embodiment according to FIG. 10, i.e., the non-capillary tube embodiment.

It will be appreciated from the foregoing that a disposable according to the present invention carries a capillary tube in spaced relationship to a needle or laser through-hole, enabling the cross sectional sizes of the capillary tube and needle (or through-hole 70) to be determined independently of one another. Furthermore, the capillary tube is slidable relative to the body of the disposable in order to be extended for reaching a sample of body fluid.

The body of the disposable carries guide bosses which are cooperable with ramps on a lancet carrier to guide the disposable during installation in order to cause a locking boss to enter a recess in the carrier. Hence, the capillary tube assumes a predetermined orientation.

Even in the absence of a capillary tube, the disposable carries an arm which functions to deactivate a locking mechanism of an arming system.

The use of a plurality of needles on the disposable allows a substantially greater sample of body fluid to be obtained without having to increase the needle gauge and thus without increasing the amount of pain experienced by a user.

Figure 13:
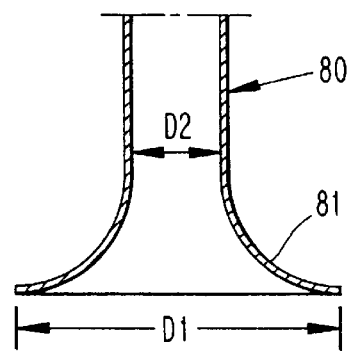
FIG. 13 is a cross-sectional view through a lower end of another embodiment of a capillary tube according to the present invention.

Depicted in FIG. 13 is an alternative shape of a lower end 81 of a capillary tube 80 wherein that lower end is flared outwardly. Consequently, as body fluid flows upwardly through the capillary tube, the speed of travel thereof increases as it travels from the wide diameter D1 of the flared lower end to the smaller diameter D2, thereby increasing the overall rate of flow of the body fluid through the capillary tube. This permits intaking the sample through diameter D1 and dispensing through diameter D2.

Figure 14:
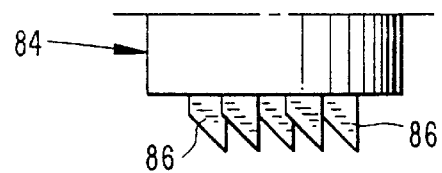
FIG. 14 is a side view of a lower end of another embodiment of a disposable lancet according to the invention.
Figure 15:
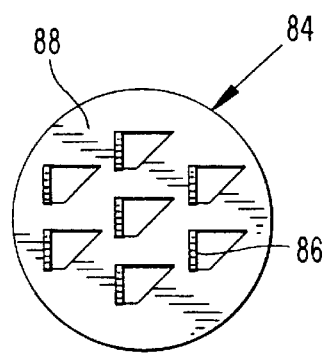
FIG. 15 is an end view of the disposable lancet depicted in FIG. 14.

Depicted in FIGS. 14, 15 is a modified lower end of a disposable lancet 84 wherein there is provided a plurality of skin lancing members 86 in the form of shallow pointed blades or barbs. Those barbs can be formed by partially cutting out sections of a metal sheet 88 and then bending those sections downwardly, as depicted in FIG. 15. The barbs produce numerous shallow incisions to increase the amount of sample, without increasing pain felt by a user.

Figure 16:
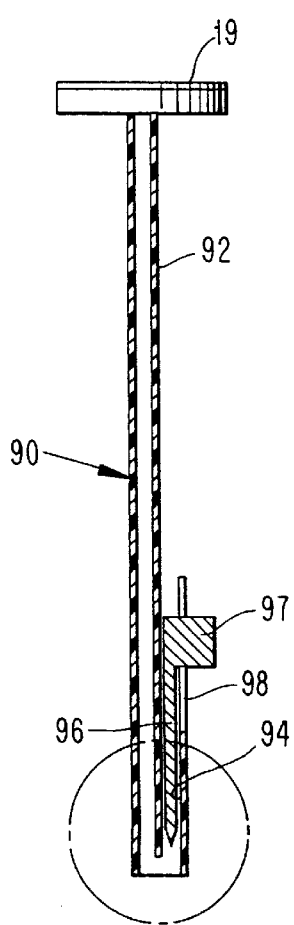
FIG. 16 is a longitudinal sectional view through another embodiment of a disposable lancet according to the present invention.
Figure 17:
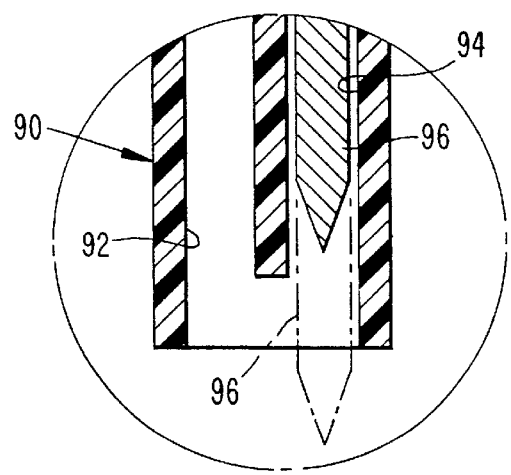
FIG. 17 is a fragmentary view of an encircled portion of FIG. 16.

FIGS. 16 and 17 depict an alternative form of disposable lancet 90 which comprises a pair of parallel passages 92, 94. A skin-lancing member 96 in the form of a needle is slidably disposed in one of the passages 94, and the other passage 92 defines a capillary tube. The needle 96 has an enlarged upper end 97 adapted to slide in a slot 98 formed along one side of the passage 94. The two passages 92, 94 communicate at 99 with one another at their adjacent forward ends. The lancet 90 can be slidably mounted in a body of a disposable, and the enlarged portion 97 of the needle would be arranged to be contacted by the driver mechanism so that, upon the triggering of the driver mechanism, the needle 96 is displaced downward relative to the capillary tube, as shown in phantom lines in FIG. 17. If desired, the needle could be spring-biased to be retracted upwardly after an incision has been made. After a drop of body fluid has been formed at the incision, the lancet 90, including the needle 96 would be pushed forwardly in the manner described earlier, whereupon the body fluid is drawn-in.

Figure 18:
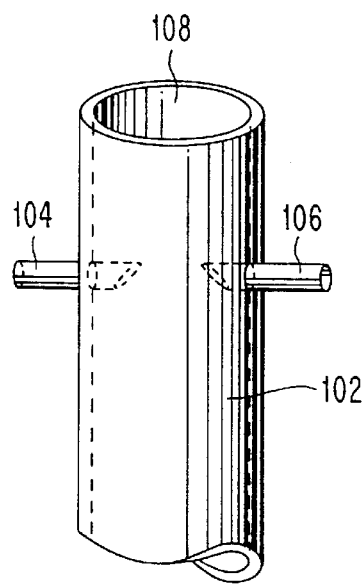
FIG. 18 is a schematic view of another embodiment of the invention wherein a capillary tube possesses a body fluid sensor.

FIG. 18 depicts a mechanism for sensing an upper level of fluid rising within a capillary tube 102. That mechanism comprises a pair of electrodes 104, 106 passing laterally through a body of the tube so as to be situated within the capillary passage 108. The electrodes would be connected in circuit to a battery and an indicator (e.g., a bulb) carried by the housing 26 so that when the upper level of body fluid rising in the passage 108 contacts the electrodes, the bulb is illuminated. The electrodes are disposed at a preselected height of the passage so that the volume of body fluid in the passage is known at the instant that the lamp is illuminated. Thus, when the lamp is illuminated, the user knows that a proper amount of sample is present in the tube and removes the tube from the incision. This prevents too much or too little sample from being taken which could otherwise require that the sampling operation be repeated.

In lieu of entering the passage 108 through a side of the tube, the electrodes could enter downwardly through an upper end of the tube. Alternatively, an electrically conductive ink could be painted around an inner surface of the passage at the preselected height.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A disposable lancing element adapted for use in a lancing device for making an incision through a user's skin, the disposable lancing element comprising:
   a skin-lancing member; and
   a capillary tube and a separate parallel tube formed unitary therewith, said parallel tube containing the skin-lancing member;
   one of the capillary tube and skin-lancing member being slidable longitudinally relative to the other.

2. The disposable lancing element according to claim 1 wherein the disposable lancing element includes a body in which the capillary tube and skin-lancing member are disposed, the capillary tube being slidable longitudinally relative to the body and adapted to be extended forwardly past the skin-lancing member.

3. The disposable lancing element according to claim 2 wherein the skin-lancing member is slidable relative to the capillary tube.

4. The disposable lancing element according to claim 2 wherein the body includes a plurality of longitudinally spaced pairs of gripping fingers frictionally gripping the capillary tube.

5. The disposable lancing element according to claim 2 wherein the body includes a plurality of circumferentially spaced, radially outwardly projecting bosses formed thereon.

6. The disposable according to claim 5 wherein one of the bosses is spaced longitudinally from two others of the bosses.

7. The disposable lancing element according to claim 1 wherein the body includes a plurality of circumferentially spaced, radially outwardly projecting bosses formed thereon.

8. The disposable lancing element according to claim 7 wherein the body includes a plurality of longitudinally spaced pairs of gripping fingers frictionally gripping the capillary tube.

9. The disposable lancing element according to claim 1, wherein the skin-lancing member constitutes a first needle, and further including at least one additional needle disposed in parallel, laterally spaced relationship to the first needle, all needles projecting from the body by equal distances.

10. The disposable lancing element according to claim 1 wherein the skin-lancing member comprises a plurality of barbs disposed in parallel, laterally spaced relationship, all barbs projecting equal distances.

11. The disposable lancing element according to claim 1 wherein a lower end of the capillary tube is flared outwardly.

12. A disposable element adapted for use in a sampling device for sampling body fluid, comprising a unitary member formed from a pair of parallel passages arranged in side-by-side relationship, a skin-lancing member slidably mounted in one of the passages, the other passage defining a capillary tube for drawing-in body fluid.

13. The disposable element according to claim 12 wherein the two passages communicate with one another at adjacent ends thereof.

* * * * *